US00PP09468P

United States Patent [19]

Meilland

[11] Patent Number: Plant 9,468

[45] Date of Patent: Mar. 12, 1996

[54] SHRUB ROSE PLANT NAMED 'MEIROZRUG'

[75] Inventor: Alain A. Meilland, Antibes, France

[73] Assignee: The Conard-Pyle Company, West Grove, Pa.

[21] Appl. No.: 495,843

[22] Filed: Jun. 28, 1995

[51] Int. Cl.[6] ..... A01H 5/00

[52] U.S. Cl. ..... Plt./1

[58] Field of Search ..... Plt./1, 22, 11

*Primary Examiner*—Howard J. Locker

*Attorney, Agent, or Firm*—Burns, Doane, Swecker & Mathis

[57] ABSTRACT

A new and distinct rugosa hybrid variety of Shrub rose plant is provided which forms substantially continuously throughout the season attractive long-lasting Rose Bengal blossoms. The new variety grows well on its own roots. The plant possesses a bushy growth habit. Also, the new variety exhibits very good disease resistance particularly with respect to Marssonina disease, and is well suited for use as attractive ornamentation in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) was the product of the artificial pollination of the 'Dagmar Hastrup' variety (non-patented in the United States) and the 'Meitulimon' variety (non-patented in the United States). The male parent (i.e., the pollen parent) of the new variety was the 'Pink Grootendorst' variety (non-patented in the United States). The parentage of the new variety can be summarized as follows:

('Dagmar Hastrup'×'Meitulimon')×'Pink Grootendorst'.

The seeds resulting from the above pollination were sown and 102 small plants were obtained which were physically and biologically different from each other. Selective study resulted in the identification of a single plant of the new variety.

The new variety can be considered to be a rugosa hybrid.

It is found that the new variety of Shrub rose plant possesses the following combination of characteristics:

(a) forms continuously substantially throughout the season attractive blossoms which are Rose Bengal in coloration,
(b) grows well on its own roots,
(c) is well suited for growing in the landscape, and
(d) exhibits very good disease resistance.

The new variety meets the needs of the horticultural industry and can be grown to particular advantage as attractive ornamentation in parks, gardens, public areas, and residential landscapes.

The new variety of the present invention has been found to undergo asexual propagation by a number of routes in France including budding, grafting and cuttings. Asexual propagation by the above-mentioned routes as performed in France has shown that the characteristics of the new variety are homogeneous and stable and are strictly transmissible from one generation to another.

The new variety has been named the 'Meirozrug' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during September while growing on their own roots outdoors as Le Cannet des Maures, Var, France.

DETAILED DESCRIPTION

Figures 1, 2, 3, 4, 5, 6, 7, 8, 9, 10, 11, 12, 13, 14, 15, 16:
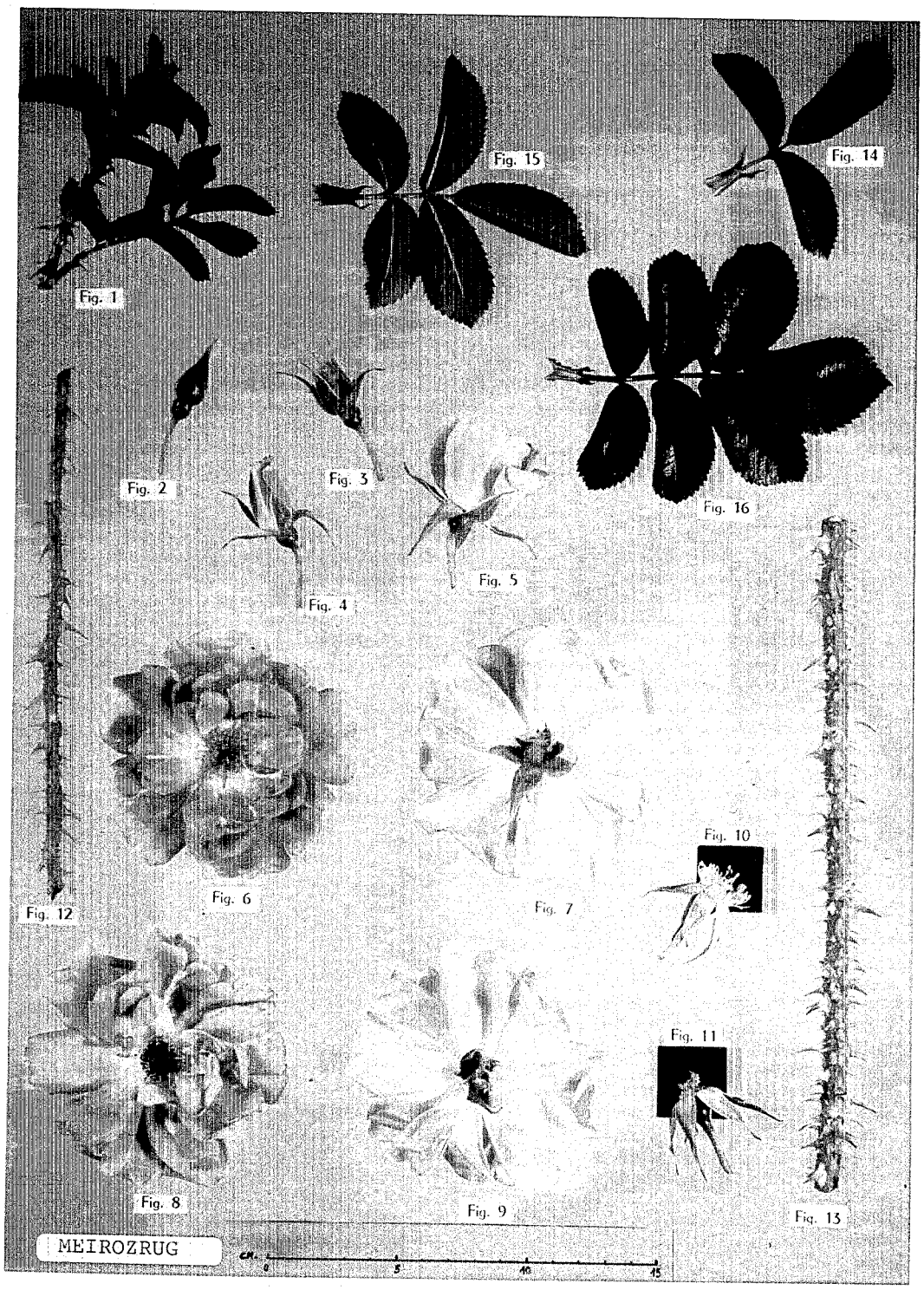
FIG. 1 illustrates a specimen of a young shoot.
FIG. 2 illustrates a specimen of a floral bud before the opening of the sepals.
FIG. 3 illustrates a specimen of a floral bud as the sepals begin to open.
FIG. 4 illustrates a specimen of a floral bud as the petals begin to open.
FIG. 5 illustrates a specimen of a flower in the course of blooming.
FIG. 6 illustrates a specimen of a open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — upper surface.
FIG. 15 illustrates a specimen of a leaf with five leaflets — under surface.
FIG. 16 illustrates a specimen of a leaf with seven leaflets — upper surface.

The chart used in the identification of the colors is that of The Royal Horticultural Society (R.H.S. Colour Chart). The terminology preceding the numbered reference to the chart has been added to indicate in more common terms the corresponding color. The description is based on the observation of two year-old specimens of the new variety while grown outdoors on their own roots during September at Le Cannet des Maures, Var, France.

Class: Shrub (rugosa hybrid).

Plant:

*Height.*—Approximately 130 to 140 cm. on average at the end of the growing season, and commonly spreads to approximately 150 to 160 cm.

*Habit.*—Bushy.

Branches:

*Color.*—Young stems: lettuce green, Yellow-Green Group 144A. Adult wood: medium green, Yellow-Green Group 146B.

*Thorns.*—Size: medium to large. Quantity: very numerous. Color: greenish coloration on young stems and adult wood.

Leaves:

*Stipules.*—Adnate, pectinate, very wide and linear.

*Petioles.*—Upper surface: striped reddish on young foliage and medium green on adult foliage with more or less glandular edges. Under surface: light green with some small thorns.

*Leaflets.*—Number: 3, 5 (most often), and 7. Shape: Oval. Serration: simple and regular as illustrated. Texture: leathery. General appearance: dense and glossy foliage. Color (young foliage): Upper surface: medium green, Green Group 138A, and more or less maculated with reddish coloration. Under surface: lighter green, Green Group 138B. Color (adult foliage): Upper surface: medium green, Green Group 138A. Under surface: light green, Green group 138B.

Inflorescence:

*Number of flowers.*—Approximately 1 to 5 flowers per stem.

*Peduncle.*—Light green with numerous pediculate glands, and approximately 3.5 cm. in length on average.

*Sepals.*—Upper surface: tomentose, and greenish in coloration. Under surface: light green with more or less appendiculated edges.

*Buds.*—Shape: oblong. Length: approximately 2.5 cm. on average. Size: medium. Color when opening: Upper surface: light Rose Bengal, Red-Purple Group 57C and sometimes with a greenish/whitish median vein. Under surface: Magenta Pink, Red-Purple Group 64C.

*Flower.*—Form: flat cupped. Diameter: approximately 11 to 13 cm. on average. Color (when opening begins): Upper surface: light Rose Bengal, Red-Purple Group 57C, and sometimes with a greenish/whitish median vein. Under surface: light Rose Bengal, Red-Purple Group 57D, and sometimes with a greenish/whitish median vein. Color (when blooming): Upper surface: light Rose Bengal, Red-Purple Group 57C, and sometimes with a greenish/whitish median vein. Under surface: light Rose Bengal, Red-Purple Group 57D, and sometimes with a greenish/whitish median vein. Color (at end of opening): Upper surface: light Rose Bengal, Red-Purple Group 57C, and sometimes with a greenish/whitish median vein. Under surface: light Rose Bengal, Red-Purple Group 57D, and sometimes with a greenish/whitish median vein. Fragrance: none. Lasting quality: long. Petal form: rounded to oval with indented tip and reflexed edges. Petal number: approximately 21 to 23 on average. Petal drop: good. Stamen number: approximately 60 to 65 on average. Anthers: Normal ochre coloration. Filaments: normal and yellowish in coloration. Pistils: approximately 33 to 41 on average. Stigmas: normal and strawlike in coloration. Styles: strawlike in coloration with a fuschine tip. Receptacle: medium green and smooth and in longitudinal section it is in the shape of a pitcher.

Development:

*Vegetation.*—Very vigorous.

*Blooming.*—Very abundant and substantially continuous.

*Aptitude to bear fruits.*—Weak.

*Resistance to diseases.*—Excellent particularly with respect to Marssonina disease.

*Resistance to frost.*—Excellent.

I claim:

1. A new and distinct variety of Shrub rose plant characterized by the following combination of characteristics:

(a) forms continuously substantially throughout the season attractive blossoms which are Rose Bengal in coloration, (b) grows well on its own roots, (c) is well suited for growing in the landscape, and (d) exhibits very good disease resistance;

substantially as herein shown and described.

* * * * *

MEIROZRUG
CM.
0
5
10
15